US008206699B2

(12) United States Patent
Goldman et al.

(10) Patent No.: US 8,206,699 B2
(45) Date of Patent: Jun. 26, 2012

(54) MYELINATION OF CONGENITALLY DYSMYELINATED FOREBRAINS USING OLIGODENDROCYTE PROGENITOR CELLS

(75) Inventors: Steven A. Goldman, Webster, NY (US); Neeta Singh Roy, New York, NY (US); Martha Windrem, West Henrietta, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 12/111,839

(22) Filed: Apr. 29, 2008

(65) Prior Publication Data

US 2008/0206209 A1    Aug. 28, 2008

Related U.S. Application Data

(63) Continuation of application No. 10/368,810, filed on Feb. 14, 2003, now abandoned.

(60) Provisional application No. 60/358,006, filed on Feb. 15, 2002.

(51) Int. Cl.
*A01N 63/00* (2006.01)
*A01N 65/00* (2009.01)
(52) U.S. Cl. ..................................... 424/93.1; 424/93.7
(58) Field of Classification Search .................. None
See application file for complete search history.

(56) References Cited

U.S. PATENT DOCUMENTS

| | | | |
|---|---|---|---|
| 6,245,564 | B1 | 6/2001 | Goldman et al. |
| 6,497,872 | B1 | 12/2002 | Weiss et al. |
| 2002/0012903 | A1 | 1/2002 | Goldman et al. |
| 2002/0061586 | A1 | 5/2002 | Goldman et al. |
| 2003/0049234 | A1 | 3/2003 | Goldman et al. |

FOREIGN PATENT DOCUMENTS

| | | |
|---|---|---|
| WO | WO 94/10292 A1 | 5/1994 |
| WO | WO 98/32879 A1 | 7/1998 |
| WO | WO 99/49014 A1 | 9/1999 |
| WO | WO 01/46384 A2 | 6/2001 |
| WO | WO 01/78753 | 10/2001 |

OTHER PUBLICATIONS

Franklin (2002) Why does remyelination fail in multiple sclerosis? Nature Reviews Neuroscience 3(9): 705-714.*
Blakemore et al., "Extensive Oligodendrocyte Remyelination Following Injection of Cultured Central Nervous System Cells into Demyelinating Lesions in Adult Central Nervous System," Dev. Neurosci. 10:1-11 (1988).
Godfraind et al., "In Vivo Analysis of Glial Cells Phenotypes During a Viral Demyelinating Disease in Mice," J. Cell Biol. 109:2405-2416 (1989).
Gumpel et al., "Myelination and Remyelination in the Central Nervous System by Transplanted Oligodendrocytes Using the Shiverer Model," Dev. Neurosci. 11:132-139 (1989).
Wang et al., "Isolation of Neuronal Precursors by Sorting Embryonic Forebrain Transfected with GFP Regulated by the Tα1 Tubulin Promoter," Nature Biotechnology 16:196-201 (1998).
Akiyama et al., "Transplantation of Clonal Neural Precursor Cells Derived from Adult Human Brain Establishes Functional Peripheral Myelin in the Rat Spinal Cord," Exp. Neuro. 167:27-39 (2001).
Espinosa De Los Monteros et al., "Remyelination of the Adult Demyelinated Mouse Brain by Grafted Oligodendrocyte Progenitors and the Effect of B-104 Cografts," Neurochemical Res. 26(6):673-682 (2001).
Gensert et al., "Endogenous Progenitors Remyelinate Demyelinated Axons in the Adult CNS," Neuron 19:197-203 (1997).
Gout et al., "Remyelination by Transplanted Oligodendrocytes of a Demyelinated Lesion in the Spinal Cord of the Adult Shiverer Mouse," Neurosci. Lett. 87:195-199 (1988).
Jeffery et al., "Behavioural Consequences of Oligodendrocyte Progenitor Cell Transplantation into Experimental Demyelinating Lesions in the Rat Spinal Cord," Eur. J. Neurosci. 11:1508-1514 (1999).
Lachapelle et al., "Transplantation of CNS Fragments into the Brain of Shiverer Mutant Mice: Extensive Myelination by Implanted Oligodendrocytes," Dev. Neurosci. 6:325-334 (1983).
Learish et al., "Intraventricular Transplantation of Oligodendrocyte Progenitors into a Fetal Myelin Mutant Results in Widespread Formation of Myelin," Annals of Neurology 46(5):716-722 (1999).
Seilhean et al., "Myelination by Transplanted Human and Mouse Central Nervous System Tissue After Long-term Cryopreservation," Acta Neuropathologica 91(1):82-88 (1989).
Windrem et al., "Progenitor Cells Derived from the Adult Human Subcortical White Matter Disperse and Differentiate as Oligodendrocytes Within Demyelinated Lesions of the Rat Brain," J. Neurosci. Res. 69:966-975 (2002).
Database Accession No. PREV200100486585 (2001).

(Continued)

*Primary Examiner* — Anne-Marie Falk
(74) *Attorney, Agent, or Firm* — LeClairRyan, a Professional Corporation

(57) ABSTRACT

One form of the present invention is directed to a method of remyelinating demyelinated axons by treating the demyelinated axons with oligodendrocyte progenitor cells under conditions which permit remyelination of the axons. Another aspect of the present invention relates to a method of treating a subject having a condition mediated by a loss of myelin or a loss of oligodendrocytes by administering to the subject oligodendrocyte progenitor cells under conditions effective to treat the condition mediated by a loss of myelin or a loss of oligodendrocytes. A further aspect of the present invention relates to an in vitro method of identifying and separating oligodendrocyte progenitor cells from a mixed population containing other mammalian brain or spinal cord cell types. This further aspect of the present invention involves removing neurons and neuronal progenitor cells from the mixed population to produce a treated mixed population. Oligodendrocyte progenitor cells are then separated from the treated mixed population to form an enriched population of oligodendrocyte progenitor cells.

12 Claims, 10 Drawing Sheets

OTHER PUBLICATIONS

Nunes et al., "Identification and Isolation of Multipotential Neural Progenitor Cells from the Subcortical white Matter of the Adult Human Brain," Nat. Med. 9(4):439-447 (2003).

Roy et al., "Identification, Isolation, and Promoter-Defined Separation of Mitotic Oligodendrocyte Progenitor Cells from the Adult Human Subcortical White Matter," J. Neurosci. 19(22):9986-9995 (1999).

Scolding et al., "Identification of A2B5-Positive Putative Oligodendrocyte Progenitor Cells and A2B5-Positive Astrocytes in Adult Human White Matter," Neurosci. 89(1):1-4 (1999).

Cao et al., "Stem Cell Repair of Central Nervous System Injury," Journal of Neuroscience Research 68:501-510 (2002).

Emerich et al., "Recent Efforts to Overcome the Blood-Brain Barrier for Drug Delivery," Exp. Opin. Ther. Patents 10 (3):279-287 (2000).

Kennea et al., "Neural Stem Cells," Journal of Pathology 197:536-550 (2002).

Mehler et al., "Progenitor Cell Biology: Implications for Neural Regeneration," Archives of Neurology 56(7):780-784 (1999).

Milward et al., "Isolation and Transplantation of Multipotential Populations of Epidermal Growth Factor-responsive, Neural Progenitor Cells from the Canine Brain," Journal of Neuroscience Research 50:862-871 (1997).

Rossi et al., "Neural Stem Cell Therapy for Neurological Diseases: Dreams and Reality," Nature Reviews Neuroscience 3:401-409 (2002).

* cited by examiner

*FIG. 3A*
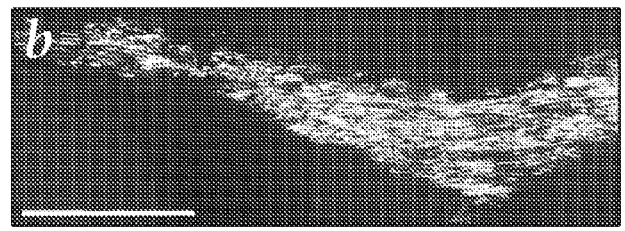
*FIG. 3B*
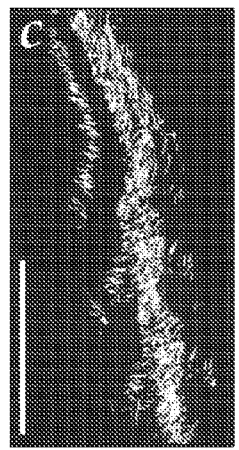         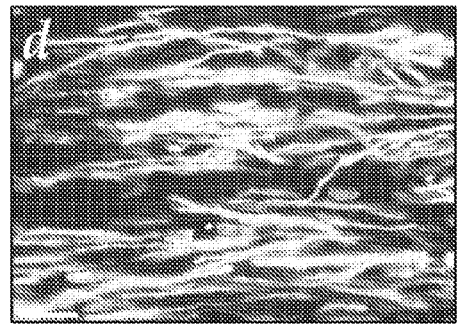
*FIG. 3C*          *FIG. 3D*

  
*FIG. 3E*  *FIG. 3F*  *FIG. 3G*
 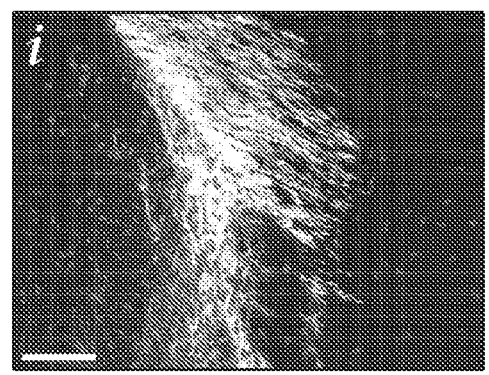
*FIG. 3H*  *FIG. 3I*

MYELINATION OF CONGENITALLY DYSMYELINATED FOREBRAINS USING OLIGODENDROCYTE PROGENITOR CELLS

This application is a continuation of U.S. patent application Ser. No. 10/368,810, filed Feb. 14, 2003, which claims the benefit of U.S. Provisional Patent Application Ser. No. 60/358,006, filed Feb. 15, 2002, which are hereby incorporated by reference in their entirety.

The subject matter of this invention was made with government support under grant number NINDS R01NS39559 awarded by National Institutes of Health. The government has certain rights in this invention.

FIELD OF THE INVENTION

The present invention is directed to the myelination of congenitally dysmyelinated forebrains using oligodendrocyte progenitor cells and to a method of treating a subject having a condition mediated by a loss of myelin or a loss of oligodendrocytes. Also disclosed is a method for the identification and separation of oligodendrocyte progenitor cells from a mixed population containing other mammalian brain or spinal cord cell types.

BACKGROUND OF THE INVENTION

A broad range of diseases, from the inherited leukodystrophies to vascular leukoencephalopathies to multiple sclerosis, result from myelin injury or loss. In the pediatric leukodystrophies, in particular, compact myelin either fails to properly develop, or is injured in the setting of toxic storage abnormalities. Recent studies have focused on the use of transplanted oligodendrocytes or their progenitors for the treatment of these congenital myelin diseases. Both rodent and human-derived cell implants have been assessed in a variety of experimental models of congenital dysmyelination. The myelinogenic potential of implanted brain cells was first noted in the shiverer mouse (Lachapelle et al., "Transplantation of CNS Fragments Into the Brain of Shiverer Mutant Mice: Extensive Myelination by Implanted Oligodendrocytes," *Dev. Neurosci* 6:325-334 (1983)). The shiverer is a mutant deficient in myelin basic protein (MBP), by virtue of a premature stop codon in the MBP gene that results in the omission of its last 5 exons (Roach et al., "Chromosomal Mapping of Mouse Myelin Basic Protein Gene and Structure and Transcription of the Partially Deleted Gene in Shiverer Mutant Mice," *Cell* 42:149-155 (1985)). Shiverer is an autosomal recessive mutation, and shi/shi homozygotes fail to develop central compact myelin. They die young, typically by 20-22 weeks of age, with ataxia, dyscoordination, spasticity, and seizures. When fetal human brain tissue was implanted into shiverers, evidence of both oligodendrocytic differentiation and local myelination was noted (Lachapelle et al., "Transplantation of Fragments of CNS Into the Brains of Shiverer Mutant Mice: Extensive Myelination by Implanted Oligodendrocytes," *Dev. Neurosci* 6:326-334 (1983); Gumpel et al., "Transplantation of Human Embryonic Oligodendrocytes Into Shiverer Brain," *Ann NY Acad Sci* 495:71-85 (1987); and Seilhean et al., "Myelination by Transplanted Human and Mouse Central Nervous System Tissue After Long-Term Cryopreservation," *Acta Neuropathol* 91:82-88 (1996)). However, these unfractionated implants yielded only patchy remyelination and would have permitted the co-generation of other, potentially undesired phenotypes. Enriched glial progenitor cells were thus assessed for their myelinogenic capacity, and were found able to myelinate shiverer axons (Warrington et al., "Differential Myelinogenic Capacity of Specific Development Stages of the Oligodendrocyte Lineage Upon Transplantation Into Hypomyelinating Hosts," *J. Neurosci Res* 34:1-13 (1993)), though with low efficiency, likely due to predominantly astrocytic differentiation by the grafted cells. Snyder and colleagues (Yandava et al., "Global Cell Replacement is Feasible via Neural Stem Cell Transplantation: Evidence from the Dysmyelinated Shiverer Mouse Brain," *Proc. Natl. Acad. Sci.* 96:7029-7034 (1999)) subsequently noted that immortalized multipotential progenitors could also contribute to myelination in shiverers. Duncan and colleagues similarly noted that oligosphere-derived cells raised from the neonatal rodent subventricular zone could engraft another dysmyelinated mutant, the myelin-deficient rat, upon perinatal intraventricular administration (Learish et al., "Intraventricular Transplantation of Oligodendrocyte Progenitors into a Fetal Myelin Mutant Results in Widespread Formation of Myelin," *Ann Neurol* 46:716-722 (1999)). These studies notwithstanding, the ability of human oligodendrocyte progenitor cell isolates to myelinate dysmyelinated brain has not hitherto been examined.

The present invention is directed to overcoming the deficiencies in the art.

SUMMARY OF THE INVENTION

One aspect of the present invention is directed to a method of remyelinating demyelinated axons by treating the demyelinated axons with oligodendrocyte progenitor cells under conditions which permit remyelination of the axons.

Another aspect of the present invention relates to a method of treating a subject having a condition mediated by a loss of myelin or a loss of oligodendrocytes by administering to the subject oligodendrocyte progenitor cells under conditions effective to treat the condition mediated by a loss of myelin or a loss of oligodendrocytes.

A further aspect of the present invention relates to an in vitro method of identifying and separating oligodendrocyte progenitor cells from a mixed population containing other mammalian brain or spinal cord cell types. This method involves removing neurons and neuronal progenitor cells from the mixed population to produce a treated mixed population. The oligodendrocyte progenitor cells are then separated from the treated mixed population to form an enriched population of oligodendrocyte progenitor cells.

Applicants have developed means by which glial and oligodendrocytic progenitor cells may be isolated from the human brain; this has allowed the use of highly enriched isolates of native human oligodendrocyte progenitor cells (OPC) for cell transplantation studies.

In this study, it was investigated whether highly enriched populations of glial progenitor cells directly isolated from the human brain might be used as a substrate for cell-based therapy of congenital dysmyelination. Specifically, it was postulated that human OPCs, derived from the fetal brain during its period of maximum oligoneogenesis, as well as from the adult brain, would be sufficiently migratory and myelinogenic to mediate the widespread myelination of a perinatal host. This showed that oligodendrocyte progenitor cells could indeed be extracted in bulk and isolated via surface antigen-based FACS from both the fetal and adult human forebrain. These cells were capable of widespread and high-efficiency myelination of the shiverer brain after perinatal xenograft. They infiltrated widely throughout the presumptive white matter, ensheathed resident murine axons, and formed antigenically and ultrastructurally compact myelin.

After implantation, the cells slowed their mitotic expansion with time, and generated neither undesired phenotypes nor parenchymal aggregates. Both fetal and adult-derived OPCs were competent to remyelinate murine axons, but important differences were noted: whereas fetal OPCs were highly migratory, they myelinated slowly and inefficiently. In contrast, adult-derived OPCs migrated over lesser distances, but they myelinated more rapidly and in higher proportions than their fetal counterparts. Thus, these isolates of human glial progenitor cells may provide effective cellular substrates for remyelinating the congenitally dys- or hypomyelinated brain. In practical terms, the choice of stage-defined cell type may be dictated by both the availability of donor material, and by the specific biology of the disease target, since both fetal and adult OPCs proved competent to effect structural remyelination.

BRIEF DESCRIPTION OF THE DRAWINGS

FIG. 1B shows the same VZ dissociate, sorted after dual immunolabeling for A2B5 (FL1, y axis) and PSA-NCAM (FL2, x axis). FIGS. 1C-D show A2B5-sorted cells expressed the oligodendrocytic sulfatide antigen recognized by monoclonal antibody O4. The A2B5$^+$/PSA-NCAM$^-$ fraction in R1R3, comprising 16.5% of the dissociate, corresponded to glial progenitor cells. Although these were able to generate both astrocytes and oligodendrocytes, they were preferentially oligoneogenic when derived at this gestational age, and were thus designated as oligodendrocyte progenitor cells (OPCs). In contrast, the R1R5 fraction, defined by the antigenic phenotype A2B5$^-$/PSA-NCAM$^+$, generated largely neurons in vitro, and was therefore defined as a neuronal progenitor pool.

FIG. 2A shows a sagittal schematic identifying the levels sampled. FIGS. 2B-E show sections corresponding to AP 1.25, 1.0, −1.0, and −2.0, in the coronal plane. Scale bar=3 mm.

FIGS. 3A-I show engrafted human OPCs myelinate an extensive region of the forebrain. FIGS. 3A-B show that extensive myelin basic protein expression by sorted human fetal OPCs, implanted into homozygote shiverer mice as neonates, indicates that large regions of the corpus callosum (FIG. 3A and FIG. 3B, 2 different mice) have myelinated by 12 weeks (MBP). FIG. 3C shows that human OPCs also migrated to and myelinated fibers throughout the dorsoventral extents of the internal capsules, manifesting widespread remyelination of the forebrain after a single perinatal injection. FIG. 3D demonstrates that myelin basic protein expression, in an engrafted shiverer callosum 3 months after perinatal xenograft, is associated with human donor cells, identified by human nuclear antigen (hNA). Both the engrafted human cells and their associated myelin were invariably found to lay parallel to callosal axonal tracts. FIGS. 3E-H show confocal optical sections of implanted shiverer corpus callosum, with human cells (hNA) surrounded by myelin basic protein (MBP). Human cells (arrows) are found within meshwork of MBP$^+$ fibers (FIG. 3E, merged image of optical sections FIGS. 3F-H, taken 1 µm apart). FIG. 3I demonstrates that OPCs were recruited as oligodendrocytes or astrocytes in a context-dependent manner, such that implanted OPCs typically matured as myelinogenic oligodendrocytes in the presumptive white matter, but as GFAP-defined astrocytes in both white and gray and white matter. This photo shows the striatocallosal border of a shiverer brain, 3 months after perinatal engraftment with human fetal OPCs (hNA). Donor-derived MBP expression is evident in the corpus callosum, while donor-derived GFAP$^+$ astrocytes predominate on the striatal side. Scale bar=200 µm. Scale: FIGS. 3A-C, 1 mm; FIG. 3D, 100 µm; FIGS. 3E-H, 20 µm; FIG. 3I, 200 µm.

FIG. 4A is a confocal micrograph showing a triple-immunostain for MBP, human ANA, and neurofilament protein. In this image, all MBP immunostaining is derived from the sorted human OPCs, whereas the NF$^+$ axons are those of the mouse host. Arrows identify segments of murine axons ensheathed by human oligodendrocytic MBP. FIG. 4B is a 2 µm deep composite of optical sections, taken through the corpus callosum of a shiverer recipient sacrificed 12 weeks after fetal OPC implantation. Shiverer axons were scored as ensheathed when the index lines intersected an NF$^+$ axon abutted on each side by MBP-immunoreactivity. The asterisk indicates the field enlarged in FIG. 4C. In FIG. 4C, at higher magnification, MBP-immunoreactivity can be seen to surround ensheathed axons on both sides. FIG. 4D is an electron micrographs of a sagittal section through the corpus callosum of an adult shi/shi homozygote. Shiverer axons typically have a single loose wrapping of myelin that fails to compact, so that major dense lines fail to form. FIGS. 4E-G are representative micrographs of 16-week old shiverer homozygotes, implanted with human oligodendrocyte progenitor cells shortly after birth. These images show resident shiverer axons with densely compacted myelin sheaths. The asterisk indicates the field enlarged in the inset. Inset, Major dense lines are noted between myelin lamellae, providing EM confirmation of myelination by engrafted human OPCs. Scale bar=FIG. 4A, 20 µm; FIG. 4B, 40 µm; FIGS. 4C-F, 1 µm.

FIGS. 5A-C show mitotic activity of engrafted progenitors falls with time. FIGS. 5A-B show BrdU incorporation by transplanted fetal human OPCs, at 4 (FIG. 5A) and 12 weeks (FIG. 5B) after xenograft. The shiverer recipients were given intraventricular injections of sorted human OPCs on postnatal day 1, then injected with BrdU (100 µg/g, i.p.) twice daily for 2 days prior to sacrifice. Mitotic human OPCs were observed as BrdU/hNA$^+$ cells (arrows). Scale bar=50 µm. FIG. 5C is a regression of the incidence of mitotically-active donor cells as a function of time after perinatal implant. The fraction of human donor cells that incorporated BrdU during the 48 hrs preceding sacrifice dropped from 42±6.1% at 4 weeks, to 8.2±2.4% at 12 weeks. Regression analysis revealed that the rate of BrdU incorporation declined with time according to the exponential regression: $y=83.4e^{-0.22x}$, with a correlation coefficient of $r=-0.87$ ($p=0.012$).

FIG. 6A shows that adult-derived human OPCs (hNA) achieved dense MBP expression by 4 weeks after xenograft. In contrast, FIG. 6B shows fetal OPCs expressed no detectable MBP-IR at 4 weeks, with such expression not noted until 12 wks. Scale=100 µm. FIGS. 4C-D are low and high magnification coronal images of the callosal-fimbrial junction of a shiverer homozygote, showing dense myelination by 12 weeks after perinatal engraftment with adult-derived hOPCs. When assessed individually, almost half of the donor cells in this recipient white matter were found to express MBP. FIG. 6E shows that a substantially higher proportion of implanted adult OPCs developed MBP expression then did fetal OPCs, when both were assessed at 12 weeks. FIG. 6F shows that fetal donor cells nonetheless engrafted more efficiently and in higher numbers than did identically-implanted adult OPCs. * indicates p<0.05; ** p<0.005, each of Student's t-test (2-tailed). Scale: FIGS. 6A-B, 100 µm, FIG. 6C, 1 mm; FIG. 6D, 30 µm.

DETAILED DESCRIPTION OF THE INVENTION

Figure 1A:
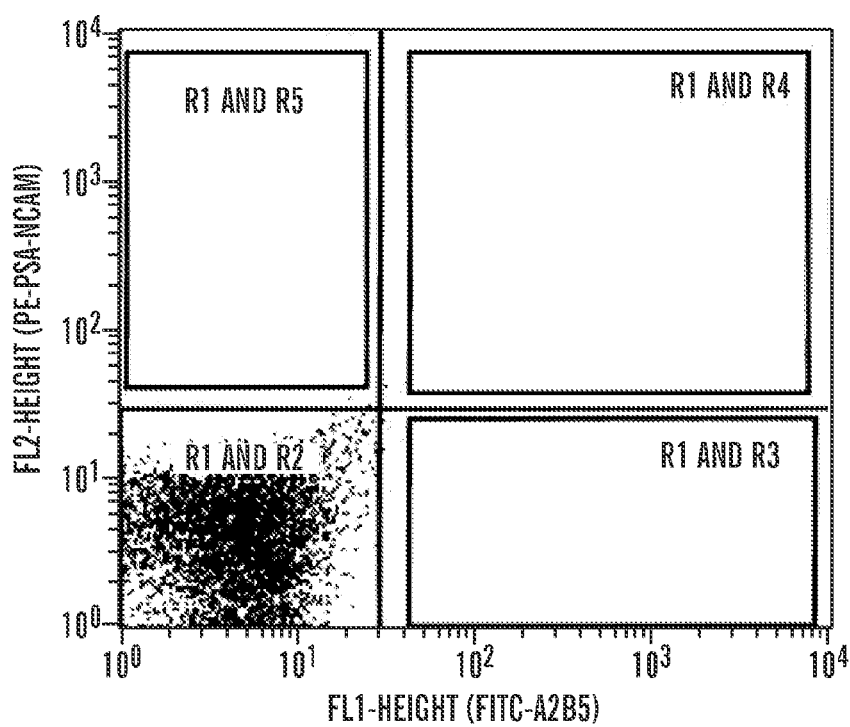
FIGS. 1A-D show fluorescence-activated sorting of fetal human oligodendrocyte progenitor cells. This shows the result of dual-color FACS of a 23 week human fetal ventricular zone dissociate, after concurrent immunostaining for both A2B5 and PSA-NCAM. The FACS plot on the left (FIG. 1A) illustrates a matched but unstained 23 week dissociate. On the right.
Figure 1B:
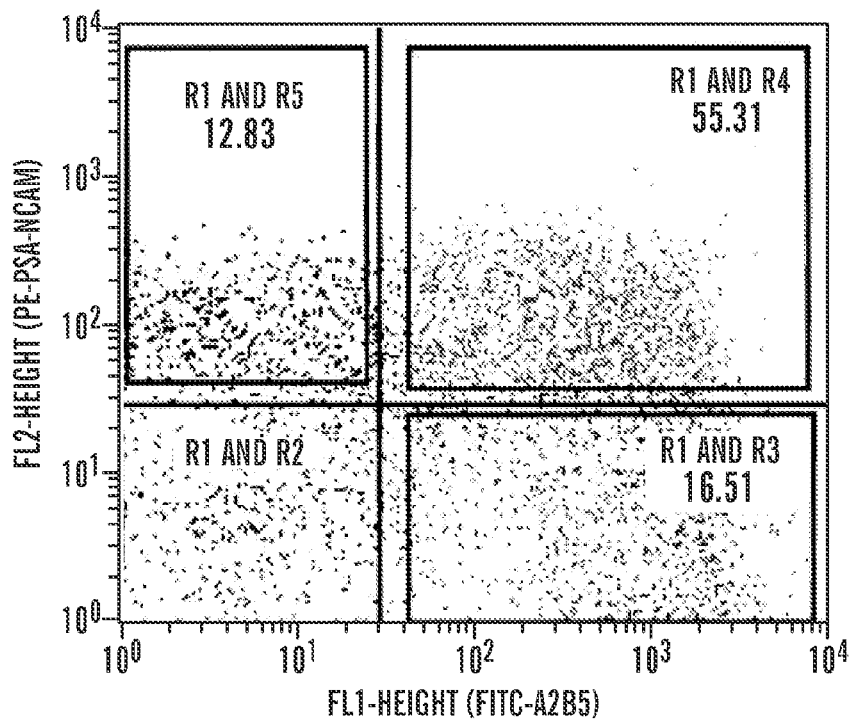
Figure 1C:
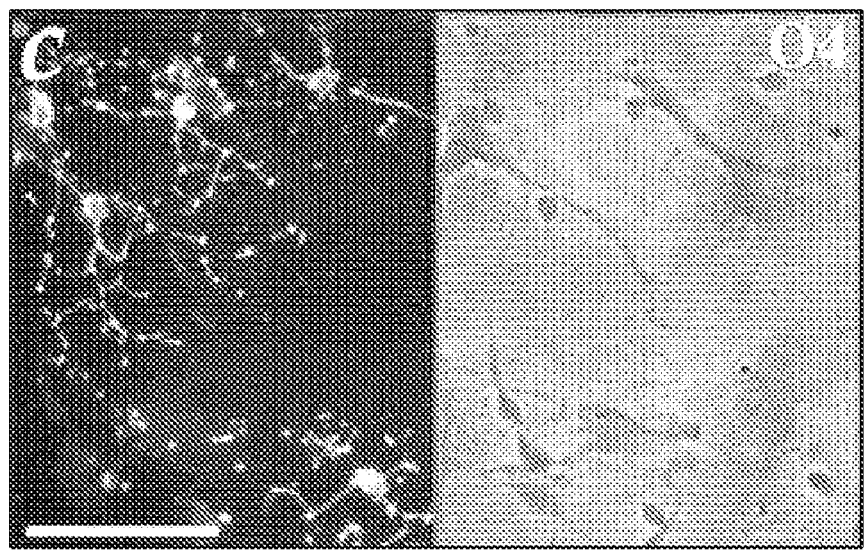
Figure 1D:
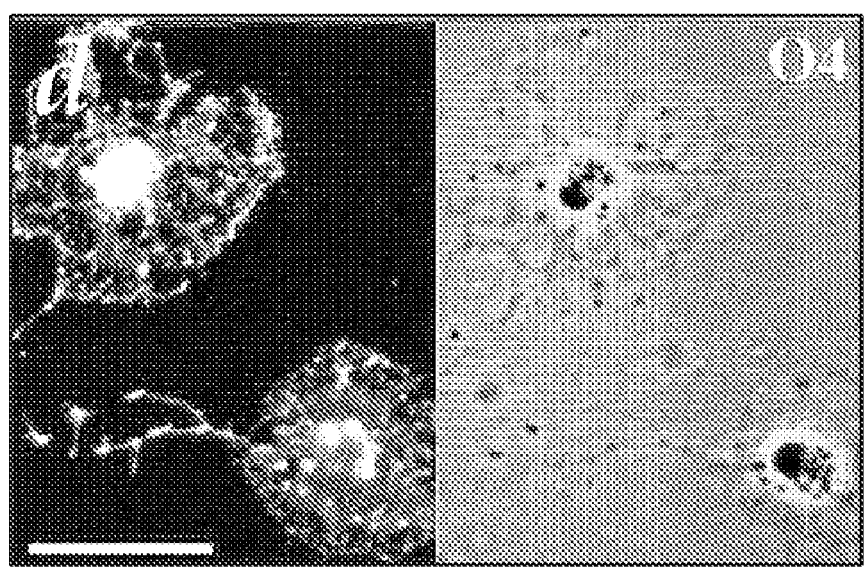
Figure 2A:
FIGS. 2A-E show fetal human OPCs migrate rapidly to infiltrate the forebrain. This composite shows the distribution of transplanted human cells 4 weeks after perinatal implantation into shiverer recipients. The human cells were localized by anti-human nuclear antigen (ANA) immunostaining; low-power fluorescence images were then collected at representative anteroposterior levels and schematized. The engrafted cells have dispersed widely throughout the forebrain, although most remain in the subcortical white matter tracts.
Figure 2B:
Figure 2C:
Figure 2D:
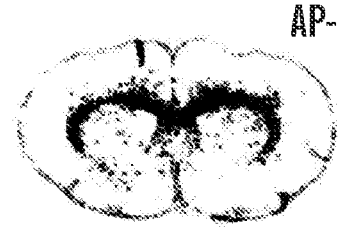
Figure 2E:

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized or recombinantly produced nucleic acid molecules).

One aspect of the present invention is directed to a method of remyelinating demyelinated axons by treating the demyelinated axons with oligodendrocyte progenitor cells under conditions which permit remyelination of the axons.

The remyelination of demyelinated axons can be carried out by:
(1) transuterine fetal intraventricular injection; (2) intraventricular or intraparenchymal (i.e. brain, brain stem, or spinal cord) injections; (3) intraparenchymal injections into adult and juvenile subjects; or (4) intravascular administration. Such administration involves cell doses ranging from $1 \times 10^5$ to $5 \times 10^7$, depending on the extent of desired remyelination.

Another aspect of the present invention relates to a method of treating a subject having a condition mediated by a loss of myelin or a loss of oligodendrocytes by administering to the subject oligodendrocyte progenitor cells under conditions effective to treat the condition mediated by a loss of myelin or a loss of oligodendrocytes.

Conditions mediated by a loss of myelin include an ischemic demyelination condition, an inflammatory demyelination condition, a pediatric leukodystrophy, mucopolysaccharidosis, perinatal germinal matrix hemorrhage, cerebral palsy, periventricular leukoinalacia, radiation-induced conditions, and subcortical leukoencephalopathy due to various etiologies.

Ischemic demyelination conditions include cortical stroke, Lacunar infarct, post-hypoxic leukoencephalopathy, diabetic leukoencephalopathy, and hypertensive leukoencephalopathy.

Inflammatory demyelination conditions include multiple sclerosis, Schilder's Disease, transverse myelitis, optic neuritis, post-vaccination encephalomyelitis, and post-infectious encephalomyelitis.

Pediatric leukodystrophy conditions include lysosomal storage diseases (e.g., Tay-Sachs Disease), Cavavan's Disease, Pelizaens-Merzbacher Disease, and Crabbe's Globoid body leukodystrophy.

An example of mucopolysaccharidosis is Sly's Disease.

Radiation-induced conditions include radiation-induced leukoencephalopathy and radiation-induced myelitis.

Etiologies causing subcortical leukoencephalopathy include HIV/AIDS, head trauma, and multi-infarct states.

Oligodendrocyte progenitor cells are administered in accordance with this aspect of the present invention in substantially the same manner as described above with regard to treatment of demyelinated axons with oligodendrocyte progenitor cells.

In one embodiment of the present invention, oligodendrocyte progenitor cells are administered to the subject after administering radiation and before demyelination has occurred. The purpose of radiation administration is to treat primary and metastatic tumors of the central nervous system.

The subject treated with oligodendrocyte progenitor cells in accordance with the present invention is preferably a human and, most preferably, an adult or post-natal human.

A further aspect of the present invention relates to an in vitro method of identifying and separating oligodendrocyte progenitor cells from a mixed population containing other mammalian brain or spinal cord cell types. This method involves removing neurons and neuronal progenitor cells from the mixed population to produce a treated mixed population. The oligodendrocyte progenitor cells are then separated from the treated mixed population to form an enriched population of oligodendrocyte progenitor cells.

The step of removing neurons and neuronal progenitor cells from a mixed population containing other mammalian brain or spinal cord cell types can be carried out by promoter based cell sorting. This procedure includes providing a mixed population of cell types from the brain and spinal cord which population includes neurons and neuronal progenitor cells as well as oligodendrocyte progenitor cells and selecting a promoter which functions in the neurons and neuronal progenitor cells, but not in the oligodendrocyte progenitor cells. A nucleic acid molecule encoding a marker protein under control of the promoter is introduced into the mixed population of cell types, and the population of neurons or neuronal progenitor cells is allowed to express the marker protein. The cells expressing the marker protein are separated from the mixed population of cells, with the separated cells being the neurons and neuronal progenitor cells. The process of selecting neurons and neuronal progenitor cells from a mixed population of cell types using a promoter that functions in the neurons and neuronal progenitor cells and a nucleic acid encoding a marker protein is described in U.S. Pat. No. 6,245,564 to Goldman et. al., which is hereby incorporated by reference in its entirety.

The neurons and neuronal progenitor cells can be separated from a mixed population containing other mammalian brain or spinal cord cell types in accordance with the present invention, as long as a promoter specific for the chosen cell is available. "Specific", as used herein to describe a promoter, means that the promoter functions only in the chosen cell type. A chosen cell type can refer to different types of cells or different stages in the developmental cycle of a progenitor cell. For example, the chosen cell may be committed to a particular adult cell phenotype and the chosen promoter only functions in that progenitor cell; i.e. the promoter does not function in adult cells. Although committed and uncommitted progenitor cells may both be considered progenitor cells, these cells are at different stages of progenitor cell development and can be separated according to the present invention if the chosen promoter is specific to the particular stage of the progenitor cell. Those of ordinary skill in the art can readily determine a cell of interest to select based on the availability of a promoter specific for that cell of interest.

Suitable promoters which are specific for neurons or neuronal progenitor cells include a MAP-1B promoter (Liu and Fischer, *Gene* 171:307-308 (1996), which is hereby incorporated by reference in its entirety), an NCAM promoter (Holst et al., *J Biol Chem* 269:22245-22252 (1994), which is hereby incorporated by reference in its entirety), an HES-5 HLH protein promoter (Takebayashi et al., *J Biol Chem* 270:1342-1349 (1995), which is hereby incorporated by reference in its entirety), an α1-tubulin promoter (Gloster, A., et al., *J Neurosci* 14:7319-7330 (1994), which is hereby incorporated by reference in its entirety), an α-internexin promoter (Ching et al., *J Biol Chem* 266:19459-19468 (1991), which is hereby incorporated by reference in its entirety), and a GAP-43 promoter (Starr et al., *Brain Res* 638:211-220 (1994), which is hereby incorporated by reference in its entirety).

Having determined the promoter specific for the neurons and neuronal progenitor cells, a nucleic acid molecule encoding a protein marker, preferably a green fluorescent protein, under the control of the promoter is introduced into a plurality of cells to be sorted.

The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from Aequorea Victoria (U.S. Pat. No. 5,491,084 to Prasher et. al., which is hereby incorporated by reference in its entirety). A plasmid designated pGFP10.1 has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 75547 on Sep. 1, 1993. This plasmid is commercially available from the ATCC due to the issuance of U.S. Pat. No. 5,491,084 on Feb. 13, 1996 in which the plasmid is described. This plasmid comprises a cDNA which encodes a green fluorescent protein (GFP) of *Aequorea victoria* as disclosed in U.S. Pat. No. 5,491,084 to Chalfie et al., which is hereby incorporated by reference in its entirety. A mutated form of this GFP (a red-shifted mutant form) designated pRSGFP-C1 is commercially available from Clontech Laboratories, Inc. (Palo Alto, Calif.).

The plasmid designated pTα1-RSGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 98298 on Jan. 21, 1997. This plasmid uses the red shifted GFP (RS-GFP) of Clontech Laboratories, Inc. (Palo Alto, Calif.), and the Tα1 promoter sequence provided by Dr. F. Miller (Montreal Neurological Institute, McGill University, Montreal, Canada). In accordance with the subject invention, the Tα1 promoter can be replaced with another specific promoter, and the RS-GFP gene can be replaced with another form of GFP, by using standard restriction enzymes and ligation procedures.

Mutated forms of GFP that emit more strongly than the native protein, as well as forms of GFP amenable to stable translation in higher vertebrates, are now available and can be used for the same purpose. The plasmid designated pTα1-GFPh has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 98299 on Jan. 21, 1997. This plasmid uses the humanized GFP (GFPh) of Zolotukhin and Muzyczka (Levy, J., et al., *Nature Biotechnol* 14:610-614 (1996), which is hereby incorporated by reference in its entirety), and the Tα1 promoter sequence provided by Dr. F. Miller (Montreal). In accordance with the subject invention, the Tα1 promoter can be replaced with another specific promoter, and the GFPh gene can be replaced with another form of GFP, by using standard restriction enzymes and ligation procedures. Any nucleic acid molecule encoding a fluorescent form of GFP can be used in accordance with the subject invention.

Standard techniques are then used to place the nucleic acid molecule encoding GFP under the control of the chosen cell specific promoter. Generally, this involves the use of restriction enzymes and ligation.

The resulting construct, which comprises the nucleic acid molecule encoding the GFP under the control of the selected promoter (itself a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled (the DNA sticks to the DEAE-dextran via its negatively charged phosphate groups, large DNA-containing particles stick in turn to the surfaces of cells (which are thought to take them in by a process known as endocytosis), and some of the DNA evades destruction in the cytoplasm of the cell and escapes to the nucleus, where it can be transcribed into RNA like any other gene in the cell); 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes so that DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; 7) naked DNA insertion; and 8) viral-mediated transformation, in which nucleic acid molecules are introduced into cells using viral vectors. Since viral growth depends on the ability to get the viral genome into cells, viruses have devised efficient methods for doing so. These viruses include retroviruses, lentivirus, adenovirus, herpesvirus, and adeno-associated virus.

As indicated, some of these methods of transforming a cell require the use of an intermediate plasmid vector. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al., *Molecular Cloning: A Laboratory Manual,* 2d Edition, Cold Spring Harbor Laboratory Press, Cold Spring Harbor, N.Y. (1989), which is hereby incorporated by reference in its entirety.

In accordance with one of the above-described methods, the nucleic acid molecule encoding the GFP is thus introduced into a plurality of cells. The promoter which controls expression of the GFP, however, only functions in the cell of interest. Therefore, the GFP is only expressed in the cell of interest. Since GFP is a fluorescent protein, the cells of interest can therefore be identified from among the plurality of cells by the fluorescence of the GFP.

Any suitable means of detecting the fluorescent cells can be used. The cells may be identified using epifluorescence optics, and can be physically picked up and brought together by Laser Tweezers (Cell Robotics Inc., Albuquerque, N. Mex.). They can be separated in bulk through fluorescence activated cell sorting, a method that effectively separates the fluorescent cells from the non-fluorescent cells.

One embodiment of separating oligodendrocyte progenitor cells from the treated mixed population, in accordance with this aspect of the present invention, is carried out by promoter based cell separation as described above, except that rather than starting with the introduction of a nucleic acid molecule encoding a fluorescent protein under control of the promoter into the entire mixed population containing mammalian brain or spinal cord cell types besides the oligodendrocyte progenitor cells, that nucleic acid molecule is introduced into the treated mixed population. In sorting out oligodendrocyte progenitor cells from the treated mixed population, a promoter specific for oligodendrocyte progenitor cells is utilized. The promoter suitable for carrying out this aspect of the present invention can be a cyclic nucleotide phosphorylase I promoter, a myelin basic protein promoter, a JC virus minimal core promoter, a proteolipid protein promoter, a qk1 promoter (i.e. the promoter for the quaking gene product), and a cyclic nucleotide phosphorylase II promoter.

As an alternative to using promoter-based cell sorting to recover oligodendrocyte progenitor cells from the treated mixed population, an immunoseparation procedure is utilized.

This involves separating cells based on proteinaceous surface markers naturally present on progenitor cells of a specific type. For example, the surface marker A2B5 is an initially expressed early oligodendrocyte marker. See Nunes et al., "Identification and Isolation of Multipotential Neural Progenitor Cells from the Adult Human White Matter," *Soc. Neurosci. Abstr.* (2001), which is hereby incorporated by reference. Using an antibody specific to that marker oligodendrocyte progenitor cells can be separated from a mixed population of cell types. Such antibodies can be labeled with a fluorescent tag to facilitate separation of cells to which they bind. Alternatively, the antibodies can be attached to paramagnetic beads so that cells which bind to the beads through the attached antibodies can be recovered by a biomagnetic separation process.

A hybridoma producing monoclonal antibodies specific to Gq ganglioside, designated A2B5 has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. CRL-01520.

The enriched population of oligodendroctye progenitor cells is at least 90% pure, preferably at least 95% pure, and most preferably at least 99% pure. The mixed population of cell types used to carry out this aspect of the present invention are preferably human cells. These cells are desirably adult or post-natal human cells.

Instead of utilizing the above-described procedure of obtaining oligodendrocyte progenitor cells by removing neurons and neuronal progenitor cells from a mixed population of brain and spinal cord cell types, leaving a treated mixed population and then separating the oligodendrocyte progenitor cells from the treated population, the oligodendrocyte progenitor cells can be recovered directly from the mixed population of brain and spinal cord cell types using promoter based cell sorting as described in U.S. Pat. No. 6,245,564 to Goldman, et. al., and U.S. patent application Ser. No. 09/282,239 to Goldman et. al., which are hereby incorporated by reference in their entirety. This method is essentially as described above, using a promoter which functions only in oligodendrocyte progenitor cells.

EXAMPLES

Example 1

Cells

Cells Tissue from late gestational age human fetuses (21 to 23 weeks) were obtained at abortion. The forebrain ventricular/subventricular zones were rapidly dissected free of the remaining brain parenchyma, and the samples chilled on ice. The minced samples were then dissociated using papain/DNAse as previously described (Keyoung et al., "Specific Identification, Selection and Extraction of Neural Stem Cells from the Fetal Human Brain," *Nature Biotechnology* 19:843-850 (2001), which is hereby incorporated by reference in its entirety), always within 3 hours of extraction. The dissociates were then maintained overnight in minimal culture media of DMEM/F12/N1 with 20 ng/ml FGF.

Example 2

Sorting

The day after dissociation, the cells were incubated 1:1 with MAb A2B5 supernatant (clone 105; ATCC, Manassas, Va.), for 30 minutes, then washed and labeled with microbead-tagged rat anti-mouse IgM (Miltenyi Biotech). All incubations were done at 4° C. on a rocker. In some instances, 2-channel fluorescence-activated cell sorting was done to define the proportions and phenotypic homogeneity of A2B5 and PSA-NCAM-defined subpopulations, using a FACSVantage SE/Turbo, according to previously described methods (Keyoung et al., "Specific Identification, Selection and Extraction of Neural Stem Cells from the Fetal Human Brain," *Nature Biotechnology* 19:843-850 (2001) and Roy et al., "In Vitro Neurogenesis by Progenitor Cells Isolated from the Adult Human Hippocampus," *Nat Med* 6:271-277 (2000), which are hereby incorporated by reference in their entirety). More typically, and for all preparative sorts for transplant purposes, magnetic separation of A2B5$^+$ cells (MACS; Miltenyi) was next performed, following the manufacturer's protocol. The bound cells were then eluted and incubated with anti-NCAM (Pharmingen) at 1:25 for 30 minutes, and labeled with anti-mouse PE at 1:200. The PSA-NCAM$^+$ population was then removed by FACS, leaving a highly enriched population of A2B5$^+$/PSA-NCAM$^-$ cells. These were maintained in vitro for 1-7 days in base media with 20 ng/ml bFGF, until implantation. See FIG. 1.

Example 3

Transplantation and Tagging

Homozygous shiverers were bred in a colony. Within a day of birth, the pups were cryoanesthetized for cell delivery. The donor cells were then implanted using a pulled glass pipette inserted through the skull, into either the corpus callosum, the internal capsule, or the lateral ventricle. The pups were then returned to their mother, and later killed after 4, 8, 12, or 16 weeks. For some experiments, recipient mice were injected for 2 days before sacrifice with BrdU (100 µg/g, as a 1.5 mg/100 µl solution), q12 hrs for 2 consecutive days.

Example 4

Immunohistochemistry

The transplanted cells were identified using anti-human nuclei antibody from Chemicon (MAB 1281), and either Rhodamine Red X-conjugated goat anti-mouse (Jackson; cat. 15-295-146) or unconjugated rabbit anti-mouse Fab (Jackson 315-007-003) followed by Rhodamine Red X-goat anti-rabbit (Jackson 111-295-144). See FIG. 2. CNP was recognized using Sternberger Monoclonal 91, MBP by either Sternberger MAb 94 or Abcam 7349 (rat); human GFAP was detected using anti-human GFAP (Sternberger MAb 21). See FIG. 3 and FIGS. 4A-C. BrdU was immunolabeled concurrently with phenotypic markers as described (Louissaint et al., "Coordinated Interaction of Angiogenesis and Neurogenesis in the Adult Songbird Brain," Neuron 34:945-960 (2002), which is hereby incorporated by reference in its entirety).

Example 5

Electron Microscopy

Animals were perfused with 4% paraformaldehyde and 0.25% glutaraldehyde in 6% sucrose phosphate buffer (sucrose-PB), post-fixed in the same solution, then sliced by Vibratome in alternating thick (400 µm) and thin (100 µm) sections. The thin sections were immunostained for MBP, while the thick sections were post-fixed in 2% paraformaldehyde and 2.5% glutaraldehye in sucrose-PB. Those thick sections adjacent to thin sections exhibiting overt MBP expression were then processed in 1% osmium-1.5% ferricyanide, 1.5% aqueous uranyl acetate, dehydrated through propylene oxide, then embedded in Epon and stained with lead citrate. See FIGS. 4D-G.

Example 6

Oligodendrocyte Progenitors can be Sorted from the Fetal Human Ventricular Wall Cells dissociated from the late second trimester human ventricular zone of 2'-23 weeks gestation were first magnetically sorted to isolate A2B5$^+$ cells. These included both oligodendrocyte and neuronal progenitor cells. Since PSA-NCAM is expressed by virtually all immature neurons at this stage of human ventricular zone development, FACS was then used to select out PSA-NCAM$^+$ cells from the larger A2B5$^+$ cell population. This removal from the A2B5$^+$ pool of NCAM-defined neuronal progenitor cells and young neurons yielded a subpopulation of A2B5$^+$/PSA-NCAM$^-$ cells, that defined our oligodendrocyte progenitor pool. By two-color fluorescence-activated cell sorting (FACS), with high-stringency control thresholds intended to limit the incidence of false positives to <0.1%, it was determined that the A2B5$^+$/PSA-NCAM$^-$ fraction constituted 15.4±4.8% of the cells in these pooled 21-23 week ventricular vvzone samples (n=5) (FIG. 1). The glial restriction and oligodendrocytic bias of these VZ progenitors was verified in vitro, as the PSA-NCAM-depleted A2B5$^+$ pool generated largely oligodendrocytes—and exclusively glia—under basal culture conditions (FIG. 1). Under these same conditions, the PSA-NCAM$^+$ fraction of A2B5$^+$ cells differentiated predominantly into neurons. Thus, two distinct methods of dual antigen immunosorting, two-color FACS and serial immunomagnetic enrichment of A2B5$^+$ cells followed by FACS depletion of PSA-NCAM$^+$ cells, each permitted the selective enrichment and high-yield extraction of oligodendrocyte progenitor cells from the 21-23 week fetal human ventricular zone. Since the latter technique—immunomagnetic separation followed by single-color FACS depletion—achieved higher net yields than direct two-color FACS, this serial approach was used for extracting and isolating the engrafted human OPC populations.

Example 7

Implanted Oligodendrocyte Progenitors Migrated Widely After Xenograft

Homozygote shi/shi mice were injected intraventricularly and intracallosally with progenitor cell isolates at P0-1. The animals were divided into subgroups that were sacrificed thereafter at 4 week intervals, at 4, 8, 12, or 16 weeks of age. None of the animals were immunosuppressed; perinatal tolerization was relied on to ensure graft acceptance, as a result of which animals were transplanted on either their day of birth or the day after (P0-1), but not beyond. These injections yielded significant and quantifiable cell engraftment (defined as >100 cells per coronal section at 3 rostrocaudal levels, sampled>100 µm apart), in 34 of the 44 neonatal mice injected for this study (25 of 33 injected with fetal hOPCs, and 9 of 11 injected with adult-derived OPCs). Although aggregates of cells were often noted in the ventricle at 4 weeks, by 12 weeks most if not all implanted cells had penetrated the callosal and fimbrial walls to invade the callosum, fimbria and capsular white matter (FIG. 2).

The OPCs typically migrated rapidly, dispersing throughout the subcortical parenchyma from the frontal white matter of the forceps minor rostrally, to the basis pontis caudally. At 4 weeks, the implanted cells, identified by their expression of human nuclear antigen (hNA), were found dispersed widely throughout the white matter, primarily within the corpus callosum, external capsule, and fimbria of the hippocampus (FIG. 2). Many nuclei, especially rostral or caudal to the injection site, appeared elongated in the orientation of the tracts, with the morphology of migrants. In addition, a distinct minority entered gray matter regions, including the septum, striatum, and olfactory bulb, and less so the neocortex. By 8 weeks, human cells extended widely throughout the forebrain, and in lesser numbers to the diencephalon. In 2 of these 8-week animals, cells were noted to enter the brainstem white matter tracts, traveling through the cerebral preduncles as far as the basis pontis. In animals allowed to survive for 12 weeks, cells were noted throughout the forebrain, though still primarily within the white matter tracts. Although human nuclei were found both throughout the forebrain, and scattered about the rostral brainstem, xenograft density was invariably greatest in the fimbrial and callosal sites of cell introduction.

Example 8

Engrafted Fetal Progenitors Matured to Express Myelin Basic Protein

The next question was whether engrafted fetal-derived progenitors matured as myelinogenic oligodendrocytes in vivo. To this end, both implanted and unimplanted control mice were immunostained for oligodendrocytic myelin basic protein (MBP), at 4, 8, and 12 weeks after implantation. Since shiverer mice express only the first exon of the MBP gene (Roach, et al., "Chromosomal Mapping of Mouse Myelin Basic Protein Gene and Structure and Transcription of the Partially Deleted Gene in Shiverer Mutant Mice," *Cell* 42:149-155 (1985), which is hereby incorporated by reference in its entirety). C-terminal-directed anti-MBP antibodies do not recognize the truncated MBP of shiverer homozygotes. As a result, any MBP immunoreactivity detected in transplanted animals necessarily derives from donor-derived oligodendrocytes. At 4 weeks, no detectable MBP was noted in 10 of 11 animals, despite widespread cell dispersion; sparse regions of nascent MBP-immunoreactivity were noted in one mouse. At 8 weeks, patchy foci of MBP expression were noted in 4 of 7 mice, typically within their callosa and hippocampal commissures. By 12 weeks though, widespread MBP expression was noted throughout the forebrain white matter tracts in 5 of 7 mice. MBP expression was particularly abundant in the fimbria posteriorly and corpus callosum anteriorly. Indeed, the corpus callosum typically expressed MBP throughout its mediolateral extent, and along its entire length in the sagittal plane (FIGS. 3A-C).

The broad distribution of myelinogenesis by engrafted cells resulted in a significant volume of myelin reconstitution in the recipient brains. For instance, in the 12-week brain shown in FIG. 3, the region of callosal myelination extended about 4 mm rostrocaudally, the length of the corpus callosum, while expanding as a trigone from a mediolateral width of 1 mm caudally to 4 mm rostrally. Given an average callosal depth of 200 μm, the effective volume of MBP-defined myelin production was 1.4 mm³. Importantly, this MBP was associated with human donor cells (FIG. 3D). To prove that MBP-IR was exclusively associated with the implanted human donor OPCs, confocal imaging was used to examine the co-localization of MBP-immunoreactivity and human nuclear antigen. Using optical sectioning with orthogonal reconstruction, it was confirmed that the MBP⁺ cells were of human origin, in that each was associated with a human soma, as defined by anti-human nuclear immunostaining (FIGS. 3E-H).

Example 9

Progenitor-Derived Oligodendrocytes Remyelinate Axons

Figure 4A:
FIGS. 4A-G show axonal ensheathment and myelin compaction by engrafted human progenitor cells.
Figure 4B:
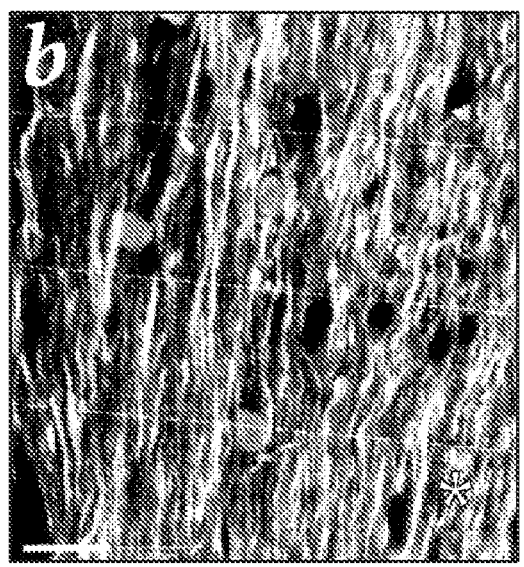
Figure 4C:
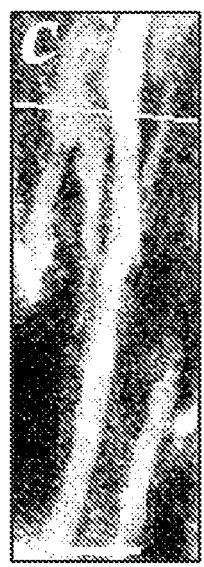
Figure 4D:
Figure 4E:
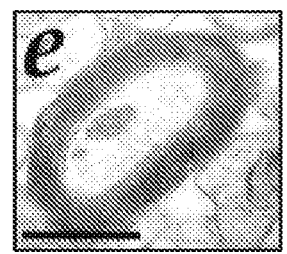
Figure 4F:
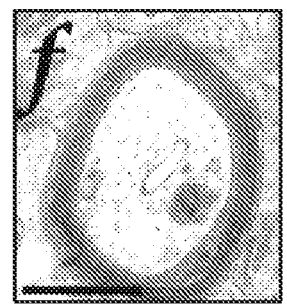
Figure 4G:
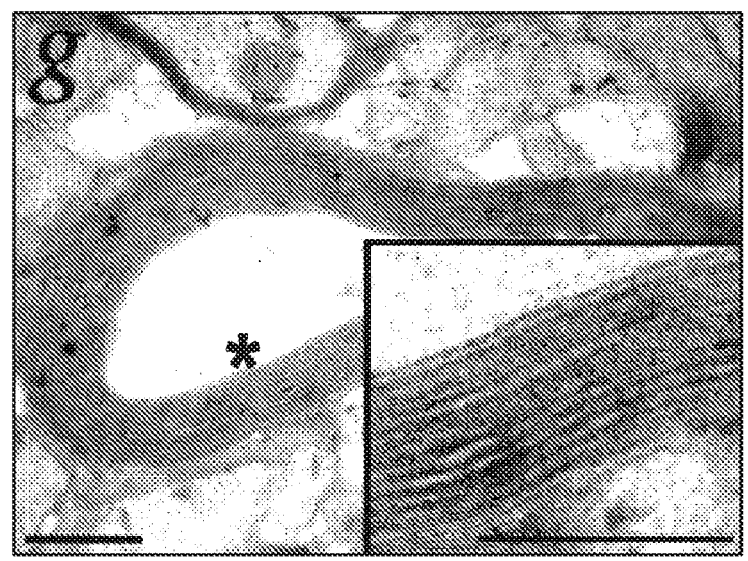

The next issue was whether the donor-derived myelin actually ensheathed host shiverer axons. To this end, both confocal imaging and electron microscopy were used to assess axonal ensheathment and myelin compaction, respectively. Confocal analysis was first done on a sample of 3 shiverer brains that were each implanted on P1 with 100,000 sorted fetal human OPCs, and then sacrificed at 12 weeks (FIGS. 4A-C). Regions of callosal MBP expression were first identified by immunolabeling fixed sections. These foci of dense MBP expression were then assessed by confocal imaging after immunolabeling for both human nuclear antigen and neurofilament protein, so as to tag donor-derived cells and host shiverer axons, respectively. By this means, human progenitors were found to have generated myelinating oligodendrocytes in great numbers. The myelin sheaths of these cells were found to be in direct apposition to, and generally completely surrounded, host axons in their immediate vicinity. Among the recipients scored, 11.9±1.6% (mean±SE) of NF⁺ host callosal axons were found to be surrounded by MBP-immunoreactivity (n=3 mice, with 3 fields scored/animal) (FIGS. 4A-C). Sampling was biased to regions of maximal callosal MBP expression, so that these numbers do not necessarily reflect the incidence of myelination in all forebrain tracts. Rather, these data simply confirm that a significant fraction of resident murine axons may be ensheathed by human myelin following perinatal engraftment of donor progenitor cells.

Next, electron microscopy was used to verify that host axons were actually ensheathed by donor-derived oligodendrocytes, and that the latter generated ultrastructurally-compact myelin. Since MBP is required for compacting consecutive layers of myelin together, its expression is required for formation of the major dense line of healthy central myelin. In the MBP-deficient shiverer, myelin is only loosely wrapped around axons, fails to exhibit more than a few wrappings, and lacks a major dense line. It was found that in the shi/shi homozygote recipients of perinatal human progenitor cell transplants, the transplanted human OPCs indeed not only myelinated, but produced compact myelin with major dense lines (FIGS. 4D-G). When assessed ultrastructurally at both 12 and 16 weeks after implant, the donor-derived myelin was confirmed to surround and ensheath host shiverer axons (FIGS. 4D-G).

This ultrastructural analysis allowed quantification of the proportion of axons myelinated by donor-derived OPCs, as a means of validating the data acquired by confocal analysis. In a sample of MBP⁺ fields (n=50), derived from 2 mice implanted on postnatal day 1 and sacrificed for histology 16 weeks later, an overall average of 7.4% of resident callosal axons were found to have donor-derived myelin sheaths (136 of 1832 scored axons), as defined by the presence of major dense lines. As in the confocal analysis, these data reflect the net efficiency of myelination achieved in callosal regions selected on the basis of their MBP-immunoreactivity, and hence defined up-front as areas of successful engraftment; the results are not intended to reflect an unbiased sample of the recipient white matter. That caveat notwithstanding, these findings demonstrate that sorted fetal human OPCs can efficiently differentiate as myelinogenic oligodendrocytes upon perinatal xenograft.

Example 10

The Proportion of Mitotically Active Donor OPCs Slowly Declined after Xenograft

Figure 5C:
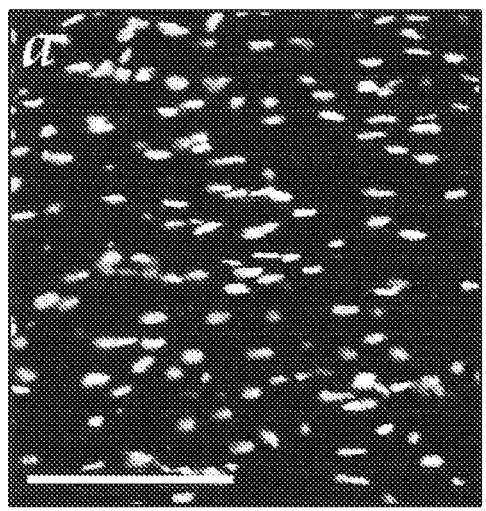
Figure 5C:
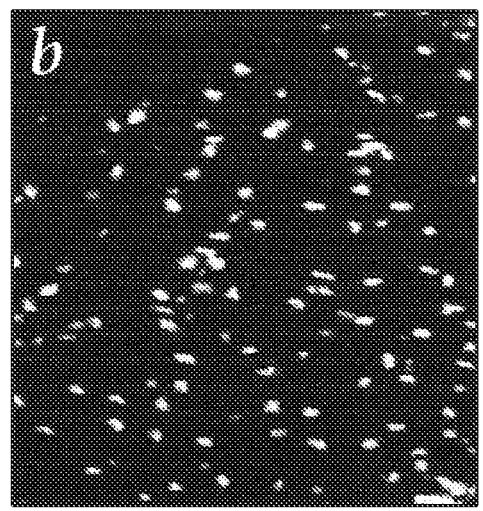
Figure 5C:
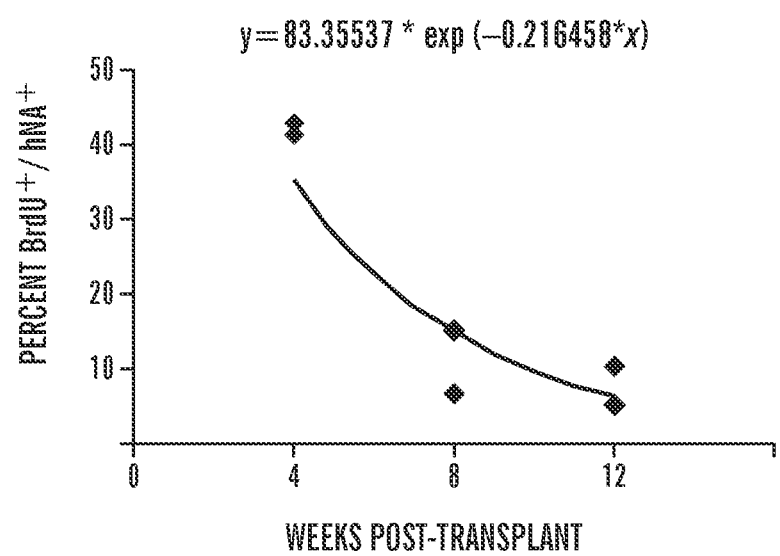

The next issue was whether implanted OPCs continued to divide after engraftment, and if so, for how long. To this end, mice were implanted with fetal hOPCs at birth (n=6), and then injected them with BrdU twice a day for two days prior to their terminal sacrifice, at 4, 8, and 12 weeks of age. Immunostaining for BrdU revealed that an average of 42±6.1% of engrafted human OPCs, implanted on the first postnatal day and defined by their expression of anti-human nuclear antigen (hNA), were still actively dividing at 4 weeks of age (FIG. 5). In contrast, by 8 and 12 weeks after implantation, the fraction of mitotic BrdW$^+$/hNA$^+$ cells among the engrafted OPCs fell to 11.2±1.6 and 8.2±2.4%, respectively. These results suggested that the implanted progenitor cells were initially mitotically active for at least the first month after engraftment, but then slowed their mitotic activity thereafter, such that less than 10% of all OPCs and progeny thereof were demonstrably cycling by their third month post-implant (FIGS. 5A-C). Regression analysis revealed a strong inverse correlation between the mitotic index of donor-derived cells and the length of time post-engraftment ($r=0.90$; $p<0.05$). Importantly, despite the preserved mitotic competence of the implanted progenitor pool, no histologic evidence of tumor formation, anaplasia, or malignant transformation was noted as long as 3 months after implantation in any of the fetal OPC-implanted mice of this study (n=34; including 9 analyzed at 16 weeks).

Example 11

Many of the Transplanted Cells Differentiated as Astrocytes

Some transplanted fetal OPCs differentiated as astrocytes, as defined by GFAP, and were noted to do so as early as 4 weeks after implantation. These GFAP$^+$ astrocytes were found intermingled with MBP$^+$ oligodendrocytes, although they typically extended over a wider area than their oligodendrocytic counterparts, which were typically restricted to white matter. Importantly, the implanted fetal hOPCs rarely differentiated as neurons in the shiverer brain: No heterotopic βIII-tubulin or MAP2-defined neurons were noted in implanted shiverer white matter at either 4, 8, or 12 weeks after implantation (n=33 total). Similarly, those cells that migrated to the septum or the striatum did not differentiate as neurons; neither did the occasional migrants that were found to enter the dorsal neocortex from the corpus callosum. Only in 2 mice, in which hNA/βIII-tubulin$^+$ neurons were found in the olfactory bulb at 4 weeks, were any human donor-derived neurons noted, likely reflecting the particularly neurogenic environment of the olfactory subependyma and bulb. More typically, those donor OPCs that invaded the gray matter typically developed as astrocytes. As a result, the donor-derived astrocytes and oligodendrocytes were typically found in sharply-demarcated geographic domains that corresponded to gray and white matter, respectively. While donor-derived astrocytes were typically more abundant in host gray matter, they were nonetheless dispersed in both gray and white matter; in contrast, donor-derived oligodendrocytes were excluded from the host gray matter (FIG. 3I). This segregation of donor-derived glial phenotypes led to sharply defined domain boundaries for the engrafted cells.

Example 12

Adult-Derived OPCs Myelinate More Rapidly than Fetal OPCs

Applicants next asked if fetal OPCs differed from their counterparts derived from the adult human brain, with respect to either their migration competence, myelinogenic capacity, or time courses thereof. To this end, 2 litters of shiverer mice were implanted on P0 with A2B5-sorted adult OPCs (n=12 mice, of whom 9 exhibited successful donor engraftment). These adult-derived hOPCs were extracted from surgical resections of normal human subcortical white matter, from which A2B5$^+$ OPCs were extracted via A2B5-directed immunomagnetic sorting (IMS), and then cultured overnight in minimal media prior to their perinatal xenograft. The implanted mice were allowed to survive for either 4, 8, or 12 weeks, then sacrificed for histology. Their brains were sectioned and stained for MBP, GFAP and anti-human nuclear antigen, as had been their fetal OPC-implanted counterparts.

It was found that fetal and adult-derived human oligodendrocyte progenitor cells differed substantially in their respective time courses and efficacy of myelinogenesis upon xenograft. Adult OPCs myelinated shiverer brain more rapidly than their fetal counterparts, achieving widespread and dense MBP expression by 4 weeks after xenograft. In contrast, substantial MBP expression by fetal OPCs was generally not observed until 12 weeks post-implant (FIGS. 6A-D).

Example 13

Figure 6A:
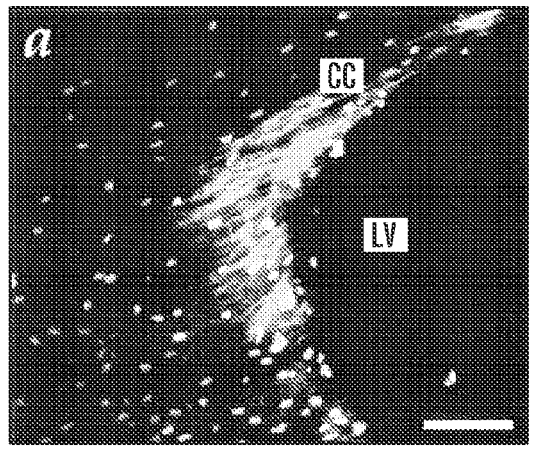
FIGS. 6A-F show fetal and adult OPCs differed substantially in their speed and efficiency of myelinogenesis.
Figure 6B:
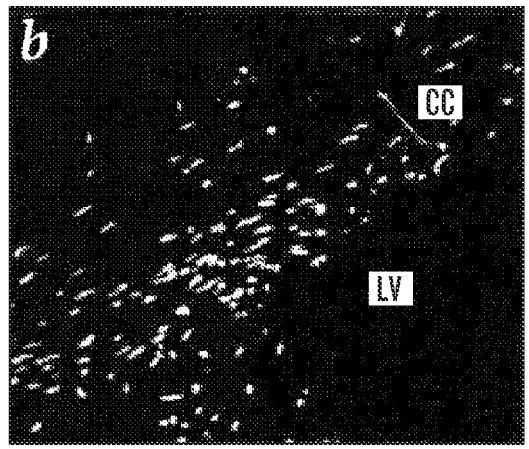
Figure 6C:
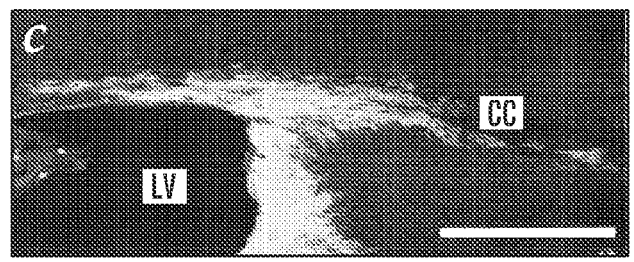
Figure 6D:
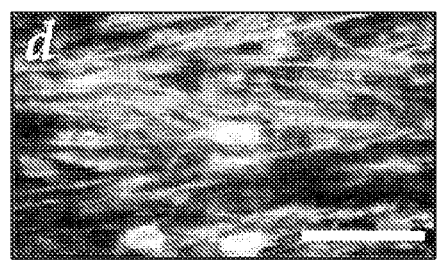
Figure 6E:
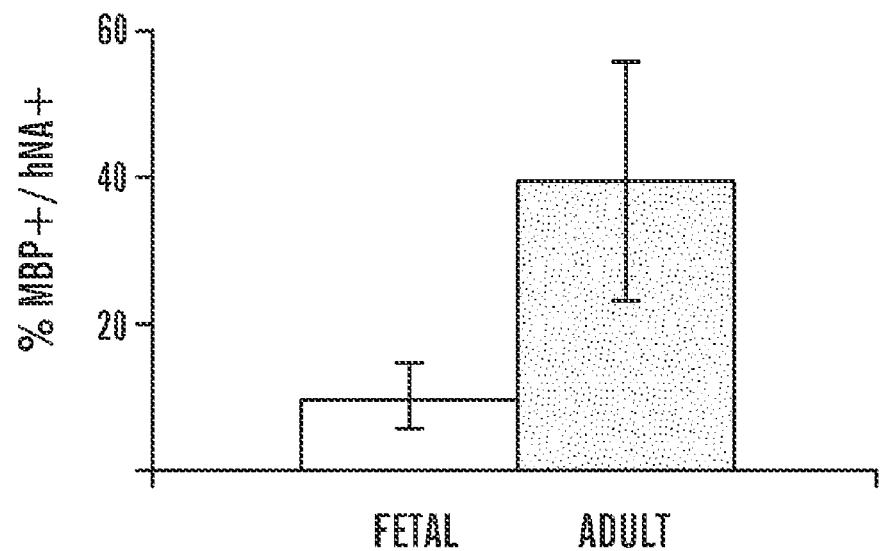
Figure 6F:
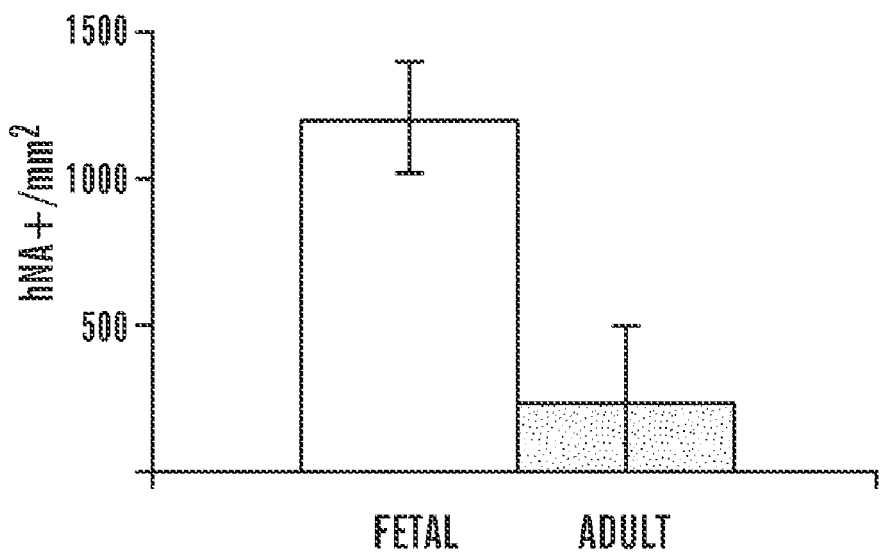

Adult OPCs Produce Myelinogenic Oligodendrocytes with Higher Efficiency than Fetal OPCs Besides maturing more quickly than fetal OPCs, adult OPCs were found to give rise to oligodendrocytes in much higher relative proportions, and with much less astrocytic co-generation, than did fetal-derived OPCs. When assessed at the midline of the recipient corpus callosum, 10.2±4.4% of fetal hNA-defined OPCs expressed MBP at 12 weeks, while virtually none did so at 4 weeks. In contrast, 39.5±16.3% of adult OPCs expressed MBP by 4 weeks after xenograft into matched recipients ($p<0.001$ by Student's 2-tailed t-test) (See FIG. 6E). Yet substantially higher numbers of fetal donor cells were found in the host brains, compared to identically-implanted adult OPCs (see FIG. 6F). Thus, fetal OPCs engrafted into shiverer recipients as well or better than adult OPCs, but those adult cells that did engraft were at least four-times more likely to mature as oligodendrocytes and develop myelin than their fetal counterparts.

Moreover while adult OPCs largely remained restricted to the host white matter, within which they generated almost entirely MBP$^+$ oligodendrocytes, fetal OPCs migrated into both gray and white matter, generating both astrocytes and oligodendrocytes in a context-dependent manner (FIG. 3I). Perhaps as a result of their greater speed and efficiency of oligodendrocytic differentiation, implanted adult OPCs and their derivatives rarely migrated beyond the bounds of the white matter, while fetal OPCs migrated widely, with their astrocytic and undifferentiated derivatives extending throughout both the forebrain gray and white matter.

It has thus been shown that highly enriched isolates of human OPCs, sorted from the highly oligoneogenic late second trimester forebrain, can successfully engraft and myelinate the shiverer mouse brain, a genetic model of perinatal leukodystrophy. Specifically, it was found that human OPCs may be selectively extracted from the late second trimester human ventricular zone in high-yield, using FACS directed at the antigenic phenotype A2B5$^+$/PSA-NCAM$^-$. When implanted to the neonatal murine forebrain, these cells reliably migrated widely throughout the forebrain, maturing in the developing white matter as both oligodendrocytes and astrocytes, and in the presumptive gray matter as astrocytes. Over a period of 4-12 weeks thereafter, the time course depending upon whether the implanted human OPCs were of fetal or adult origin, the donor-derived oligodendrocytes matured to produce myelin, which led to the widespread myelination of resident axons within the shiverer subcortex. This myelination, verified as such by both confocal and ultrastructural analysis, was geographically extensive, and extended throughout all white matter regions of the telencephalon.

Example 14

High-Yield Purification of Native Human Forebrain OPCs

Applicants had previously found that FACS based upon GFP expression driven by the early oligodendrocytic CNP2 promoter could be used to isolate oligodendrocyte progenitor cells from the adult human white matter (Roy et al., "Identification, Isolation, and Promoter-Defined Separation of Mitotic Oligodendrocyte Progenitor Cells from the Adult Human Subcortical White Matter," *Neurosci* 19:9986-9995 (1996), which is hereby incorporated by reference in its entirety). These cells expressed the surface ganglioside recognized by the A2B5 antibody, which could also be used to selectively extract the population from the adult white matter (Windrem et al., "Progenitor Cells Derived from the Adult Human Subcortical White Matter Disperse and Differentiate as Oligodendrocytes Within Demyelinated Regions of the Rat Brain," *J. Neurosci. Res.* 69:966-975 (2002), which is hereby incorporated by reference in its entirety). However, A2B5 recognizes young neurons as well as oligodendrocytes (Eisenbarth et al., "Monoclonal Antibody to a Plasma Membrane Antigen of Neurons," *Proc. Natl. Acad. Sci.* 76:4913-17 (1979) and Raff et al., "Two Types of Astrocytes in Cultures of the Developing Rat White Matter: Differences in Morphology, Surface Gangliosides, and Growth Characteristics," *J. Neurosci.* 3:1289-1300 (1983), which are hereby incorporated by reference in their entirety). Thus, although A2B5-based separation may be effectively used to extract OPCs from the adult white matter, which is largely free of neurons, it is not adequate for doing so from fetal brain, in which A2B5$^+$ neurons are abundant. To address this issue, applicants double-sorted against both A2B5 and polysialylated N-CAM (PSA-NCAM), which is ubiquitously expressed by young neurons. By excluding PSA-NCAM$^+$ cells from the A2B5-sorted sample, a population of cells that gave rise almost exclusively to glia and principally to oligodendrocytes was isolated. This A2B5$^+$/PSA-NCAM$^-$ phenotype reliably identified an abundant pool of mitotic oligodendrocyte progenitors in the fetal human brain, which appeared analogous to the adult progenitor pool recognized by P/CNP2:hGFP and A2B5 alone. The combination of this high-yield technique for high-grade enrichment of OPCs, combined with the great abundance of OPCs in the highly oligoneogenic 21-23 weeks human ventricular zone, provided for the first time significant quantities of human oligodendrocyte progenitor cells, isolated in a purity and quality appropriate for therapeutic implantation.

Example 15

Differential Dispersion During Migration

In these experiments, highly-enriched pools of human OPCs were implanted into the brains of neonatal shiverer mice to assess their migratory activity, oligodendrocytic maturation, and efficiency of myelinogenesis. It was found that the sorted OPCs proved highly migratory, and reached most structures of the forebrain within 4-8 weeks of implantation (FIG. 2). Yet the dispersal patterns of their two derivative phenotypes, oligodendrocytes and astrocytes, differed considerably in their shiverer hosts. Whereas oligodendrocytes were abundant closer to the injection site, astrocytes dispersed more widely, broadly invading the forebrain gray matter. This may have reflected a selection process, with astroglia migrating more rapidly or aggressively than their oligodendrocytic counterparts. Similarly, the A2B5$^+$/PSA-NCAM$^-$ defined pool may be heterogeneous, such that lineage-restricted oligodendrocyte progenitors may remain near the site of injection, while less differentiated, more motile progenitors might continue to migrate during early expansion, differentiating preferentially as astrocytes upon the cessation of migration. Alternatively, the preferential migration of astroglia to gray matter parenchymal sites may reflect a geographic restriction against oligodendrocytic infiltration beyond the white matter compartment. It is likely that each of these considerations contributes to the different dispersion patterns noted.

Example 16

Persistence of Uncommitted Progenitors

At all timepoints sampled, large numbers of nestin$^+$/hNA$^+$ cells were noted that failed to express either astrocytic or oligodendrocytic antigens, and which instead seemed to remain in the host parenchyma as persistent progenitors. The incidence of these uncommitted nestin$^+$/GFAP$^-$/MBP$^-$ donor cells was clearly higher in the fetal than adult-derived grafts. Nonetheless, while most adult-derived OPCs matured as oligodendrocytes, or less so astrocytes, a large fraction remained nestin$^+$/GFAP$^-$/MBP$^-$ (FIG. 4A). Such uncommitted cells may constitute both a blessing and a curse in an engrafted recipient—they likely comprise a source of progenitors that can be further stimulated in vivo, whether pharmacologically or in response to demyelinative injury, to give rise to myelinogenic oligodendrocytes. On the other hand, they might also represent a potential source of ectopic neurons upon redirection to a neuronal fate; conceivably, they might also constitute a reservoir of mitotically competent cells for later neoplastic transformation (that being said, applicants have never noted tumor formation in any recipient of human brain-derived progenitor cells). Thus, the persistence in engrafted recipients of uncommitted progenitors, whose phenotypic fate and potential for later expansion remain unclear, provides a cautionary note that must be considered prior to any use of sorted oligodendrocyte progenitor cells in clinical therapeutics.

Example 17

Clinical Utility

The above results suggest that congenital dysmyelination, like adult demyelination (Windrem et al., "Progenitor Cells Derived from the Adult Human Subcortical White Matter Disperse and Differentiate as Oligodendrocytes Within Demyelinated Regions of the Rat Brain," *J. Neurosci. Res.* 69:966-975 (2002), which is hereby incorporated by reference in its entirety), may be an appropriate target for cell-based therapy, using allografts of directly isolated human CNS progenitor cells. In the present study, the effect of donor engraftment and myelination upon either the disease phenotype or survival of the recipient mice was not assessed. However, since the shiverer CNS is dysmyelinated throughout its CNS, it is likely that broad myelination of the brainstem and spinal cord, as well as of the brain, will be required for significant therapeutic benefit. Such widespread graft-associated myelination may require higher cell doses than those used in this study, delivered at multiple injection sites spanning the neuraxis. In this regard, the concurrent injection of higher cell doses into both the cisterna magna and forebrain ventricles may yield substantially wider donor cell engraftment and myelinogenesis than achievable through forebrain injection alone (Mitome et al., "Towards the Reconstruction of Central Nervous System White Matter Using Precursor Cells," *Brain* 124:2147-2161 (2001), which is hereby incorporated by reference in its entirety).

Such a strategy of cell-based myelination of a dysmyelinated host might be of special benefit when directed at newborn recipients, given the immunological tolerance to alloantigens introduced to neonatal recipients (Ridge et al., "Neonatal Tolerance Revisited: Turning on Newborn T Cells With Dendritic Cells," *Science* 271:1723-1726 (1996); Roser, B., "Cellular Mechanisms in Neonatal and Adult Tolerance," *Immunol. Rev.* 107:179-202 (1989); and Witzke et al., "Induction of Tolerance to Alloantigen," *Rev. Immunogenet.* 1:374-386 (1999), which are hereby incorporated by reference in their entirety). None of the animals received immunosuppressive therapy, and there was no evidence of immune rejection of the engrafted human cells. This was in marked contrast to implantation of human OPCs to the adult rat brain, where immune rejection of implanted cells was a sufficient problem to mandate high-dose sustained immunosuppression using cyclosporin (Windrem et al., "Progenitor Cells Derived from the Adult Human Subcortical White Matter Disperse and Differentiate as Oligodendrocytes Within Demyelinated Regions of the Rat Brain," *J. Neurosci. Res.* 69:966-975 (2002), which is hereby incorporated by reference in its entirety). As such, congenital diseases such as the hereditary leukodystrophies, including Krabbe's, Canavan's and Tay-Sach's among others, as well as perinatal germinal matrix hemorrhages and the cerebral palsies, may all prove viable targets for cell-based therapeutic remyelination.

Example 18

Distinct Features of Fetal and Adult Progenitors

It was surprising to discover that fetal and adult oligodendrocyte progenitor cells differed fundamentally in their time course and efficiency of myelinogenesis (FIG. 6). Adult-derived OPCs were able to mature and myelinate much more quickly, and with higher efficiency and in greater relative proportions, than their analogously isolated fetal counterparts. Whereas fetal OPCs were generally not observed to myelinate until 8 weeks after implant, and to not exhibit substantial myelination before 12 weeks, adult OPCs matured and myelinated quickly—almost invariably by 4 weeks. Besides myelinating much more rapidly than their fetal counterparts, adult OPCs matured as myelinogenic oligodendrocytes with much higher efficiency—that is, in much higher relative proportions, and with much less astrocytic co-generation—than fetal-derived progenitors. As a result of their more efficient, rapid, and robust myelination, adult-derived OPCs might appear to constitute a more immediately useful therapeutic vector than the otherwise analogous, and similarly-derived fetal-derived OPCs. This observation has significant implications with regards to the therapeutic application of these cells, most particularly in regards to the disease targets that one might choose to approach with fetal and adult OPCs. Fetal cells might be appropriate therapeutic vectors for preventing dysmyelination in developing brains otherwise destined for congenital dysmyelination, in which endogenous myelination is both slow and delayed. In contrast, diseases of acquired demyelination, in which extant myelin is lost and mature axons denuded, may require the rapid maturation and myelination offered by adult-derived progenitors.

Thus, human oligodendrocyte progenitor cells may be isolated from both the fetal and adult human brain, each in a purity and yield that permit engraftment for the purpose of therapeutic remyelination. Fetal and adult-derived phenotypes differ, in that whereas fetal OPCs migrate more extensively, adult OPCs generate myelin more rapidly, and with less adventitious astrocytic production. Thus, the two stage-defined phenotypes may prove suited to quite distinct disease targets and therapeutic strategies. Nonetheless, both fetal and adult-derived purified human OPCs may be used to achieve widespread and efficient myelination of the congenitally dysmyelinated mammalian brain.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of treating a subject having a leukodystrophy comprising:
administering to the subject A2B5$^+$/PSA-NCAM$^-$ oligodendrocyte progenitor cells derived from the same species as the subject via intraventricular, intracallosal, or intraparenchymal administration to the brain, brain stem or spinal cord under conditions effective to treat the leukodystrophy, wherein the A2B5$^+$/PSA-NCAM$^-$ oligodendrocyte progenitor cells are separated from a mixed population of mammalian brain or spinal cord cells.

2. The method according to claim 1, wherein the subject is a human.

3. The method according to claim 2, wherein the subject is a post-natal human.

4. The method according to claim 2, wherein the subject is an adult human.

5. The method according to claim 1, wherein the method is carried out in the brain.

6. The method according to claim 1, wherein the method is carried out in the spinal cord.

7. The method according to claim 2, wherein the subject is a fetal human.

8. The method according to claim 1, wherein neuronal progenitor cells have also been removed from the mixed population.

9. The method according to claim 1, wherein said administering is carried out by intraventricular administration.

10. The method according to claim 1, wherein said administering is carried out by intracallosal administration.

11. The method according to claim 1, wherein said administering is carried out by intraparenchymal administration.

12. The method according to claim 1, wherein said administering is carried out by transuterine fetal intraventricular injection.

* * * * *